(12) United States Patent
González Ojer et al.

(10) Patent No.: US 9,205,149 B2
(45) Date of Patent: Dec. 8, 2015

(54) PHARMACEUTICAL TOPICAL COMPOSITION OF MUPIROCIN

(75) Inventors: Carlos González Ojer, Pamplona (ES); Beatriz Goñi Allo, Pamplona (ES); Fiona Pastor Fernández, Getxo (ES); Cayetana Yárnoz De Miguel, Pamplona (ES)

(73) Assignee: LABORATORIOS OJER PHARMA, S.L., Pamplona (Navarra) (ES)

( * ) Notice: Subject to any disclaimer, the term of this patent is extended or adjusted under 35 U.S.C. 154(b) by 0 days.

(21) Appl. No.: 13/879,008

(22) PCT Filed: Oct. 19, 2011

(86) PCT No.: PCT/EP2011/068242
§ 371 (c)(1),
(2), (4) Date: Jun. 18, 2013

(87) PCT Pub. No.: WO2012/052472
PCT Pub. Date: Apr. 26, 2012

(65) Prior Publication Data
US 2013/0267587 A1     Oct. 10, 2013

(30) Foreign Application Priority Data
Oct. 20, 2010 (EP) .................................... 10382274

(51) Int. Cl.
| | | |
|---|---|---|
| *A01N 43/16* | (2006.01) | |
| *A61K 31/35* | (2006.01) | |
| *A61K 47/32* | (2006.01) | |
| *A61K 9/00* | (2006.01) | |
| *A61K 9/06* | (2006.01) | |
| *A61K 31/351* | (2006.01) | |
| *A61K 47/46* | (2006.01) | |

(52) U.S. Cl.
CPC ............... *A61K 47/32* (2013.01); *A61K 9/0014* (2013.01); *A61K 9/06* (2013.01); *A61K 31/351* (2013.01); *A61K 47/46* (2013.01)

(58) Field of Classification Search
None
See application file for complete search history.

(56) References Cited

U.S. PATENT DOCUMENTS

| 2005/0123576 A1* | 6/2005 | Lavon et al. .................. 424/401 |
| 2007/0280891 A1* | 12/2007 | Tamarkin et al. ................ 424/47 |
| 2008/0299220 A1 | 12/2008 | Tamarkin et al. |

FOREIGN PATENT DOCUMENTS

| EP | 0231621 A2 | 8/1987 |
| EP | 0251434 A2 | 1/1988 |
| EP | 1174133 A1 | 1/2002 |
| WO | WO98/23291 A1 | 6/1998 |
| WO | WO2004010988 A1 | 2/2004 |
| WO | WO2008/094002 A1 | 8/2008 |

OTHER PUBLICATIONS

Remington: "The Science and Practice of Pharmaceutical," 21st Edition (2006) at p. 351.*
Organisation of Economic co-operation and Development, Guidance Document for the conduct of Skin Absorption Studies, OECD Environmental Health and Safety Publications Series on Testing and Assessment, Mar. 5, 2004, pp. 1-31, No. 28, Organisation of Economic co-operation and Development, Paris, France.
Office of Training and Communications, Division fo Communications Management, The Drug Information Branch, HFD-210, Guidance for Industry Nonsterile Semisolid Dosage Forms, Scale-Up and Postapproval Changes: Chemistry, Manufacturing, and Controls; In vitro Release Testing and In Vivo Bioequivalence Documentation, May 1997, pp. 1-40, U.S. Department of Health and Human Services, Food and Drug Administration, Center for Drug Evaluation and Research (CDER), Rockville, MD.
John Gisby et al., Efficacy of a New Cream Formulation of Mupirocin: Comparison with Oral and Topical Agents in Experimental Skin Infections, Antimicrobial Agents and Chemotherapy, Feb. 2000, pp. 255-260, vol. 44, No. 2, American Society for Microbiology, Washington, D. C.
MJ Lawrence, Medium-chain triglycerides, Pharmaceutical Excipients, Aug. 22, 2005, pp. 1-6, Electronic version, 2006 (the year of publication is sufficiently earlier than the effective U.S. filing date and any foreign priority date so that the particular month of publication is not in issue), Pharmaceutical Press and American Pharmacists Association, London, England. http://localhost:2961/excipents/current/1000302966.htm, accessed Jul. 10, 2010.
International Search Report and Written Opinion of the International Searching Authority, Search Report, Application No. PCT/EP2011/068242 issued by the European Patent Office, Rijswijk, Netherlands, dated Jan. 23, 2012.

* cited by examiner

*Primary Examiner* — Craig Ricci
*Assistant Examiner* — Jared D Barsky
(74) *Attorney, Agent, or Firm* — Peter B. Scull; Hamilton, DeSanctis & Cha LLP

(57) ABSTRACT

Anhydrous topical gel composition of mupirocin or its salts comprising: a) a lipophilic base selected from the group consisting of petrolatum, medium-chain triglycerides, isopropyl myristate and mixtures thereof; b) a bioadhesive selected from the group comprising polyvinylpyrrolidone and polymethacrylates; and c) a solvent selected from the group comprising ethanol, propanol, and isopropanol; which is stable and shows an increased residence time of the active ingredient in the skin, resulting in an improved clinical effect in the treatment of bacterial skin infections while maintaining the safety profile of the commercial pharmaceutical product.

1 Claim, 1 Drawing Sheet

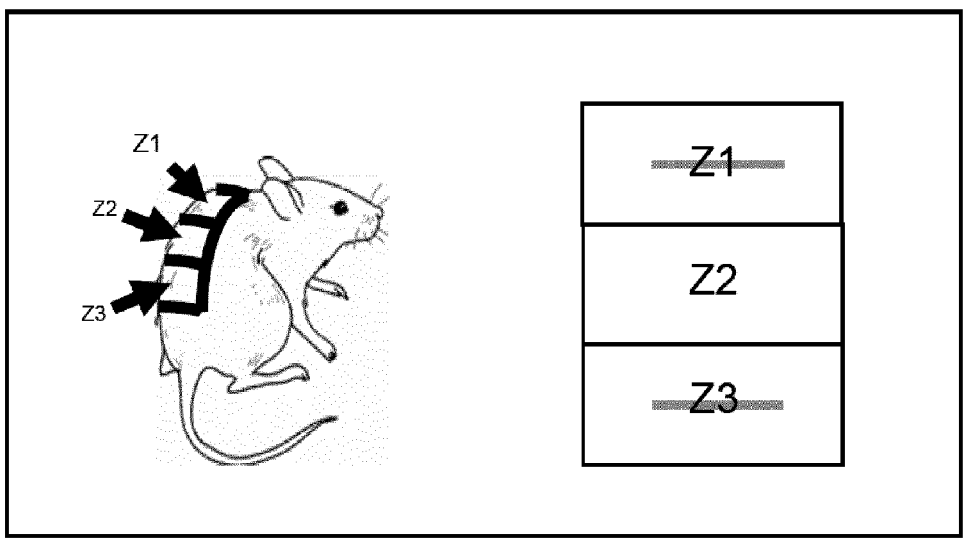

PHARMACEUTICAL TOPICAL COMPOSITION OF MUPIROCIN

The present invention refers to the field of pharmacy. More specifically, the invention relates to the development of new pharmaceutical compositions.

BACKGROUND ART

Mupirocin or pseudomonic acid A is also known by its chemical name 9-[(E)-4-[(2S,3R,4R,5S)-3,4-dihydroxy-5-[[(2S,3S)-3-[(2S,3S)-3-hydroxybutan-2-yl]oxiran-2-yl]methyl]oxan-2-yl]-3-methylbut-2-enoyl]oxynonanoic acid and CAS No. 12650-69-0. Its chemical structure is:

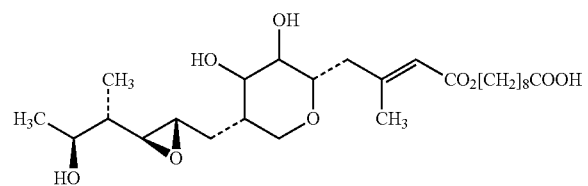

Mupirocin is a antibiotic agent produced by fermentation of *Pseudomonas fluorescens*. Mupirocin is active against a wide range of gram-positive and certain gram-negative bacteria by the inhibition of bacterial protein synthesis by reversibly and specifically binding to bacterial isoleucyl transfer-RNA synthetase.

Mupirocin is currently marketed by Smithkline Beecham in the pharmaceutical form of an ointment, a cream, and a nasal oinment under the tradename of Bactroban. Bactroban is approved in the European Union (EU) and the United States of America as a topical antibiotic. In the EU, mupirocin is indicated for the treatment of acute primary bacterial skin infections, e.g. impetigo and folliculitis, and secondary bacterial skin infections, e.g. dermatitis, due to organisms which are sensitive to mupirocin.

Both topical compositions of Bactroban for use on the skin, i.e. Bactroban ointment and Bactroban cream, are formulated with hydrophilic ointment bases. Bactroban ointment is formulated with a water soluble ointment base which consists in a mixture of polyethyleneglycols and Bactroban Cream is formulated with a water-removable water in oil cream base.

Mupirocin and its commercial salts, e.g. mupirocin calcium, are mainly hydrophobic and, generally, mupirocin compositions which are based on hydrophilic bases or aqueous mediums tend to inestability.

Mupirocin has also been formulated with lipophilic bases. Unfortunately, they are not always suitable for dissolving mupirocin. Generally, dissolution of the active ingredient is more desirable than suspension to increase clinical effect of topical compositions. Dissolution improve the diffusion of the active ingredient from the composition to the treatment site. EP251434A2 discloses topical lipophilic ointments and water based creams of mupirocin and its calcium salt. As reported in the Examples, the lipophilic ointments provided were unable to dissolve more than 1% of the active ingredient in the composition.

Other compositions of mupirocin have also been disclosed in the art with the aim to improve mupirocin stability in the composition. For instance, EP1174133A1 discloses topical compositions based in the use of a hydrophobic phase, in particular a composition comprising amorphous mupirocin calcium, a hydrophobic phase, and hexylene glycol as solvent.

Although topical creams and ointments comprising an active ingredient are widely used, their utility decrease when the composition is required to stay in the site of treatment for a long time. The clinical effect of topical treatments are impaired because compositions are easily removed from the application site due to transpiration, humidity, and erosion, resulting in the need of increasing the daily applications of the composition in the treatment site and, thus, difficulting patient compliance of the treatment.

Bioadhesive and film-forming compositions, which remain in the site of treatment for longer time, have been developed to improve clinical effect of topical compositions and patient compliance. For instance, WO199823291A1 discloses general film-forming pharmaceutical compositions comprising delivery rate modulating polymers.

WO200410988A1 discloses aqueous compositions of mupirocin with ethylcellulose as a rate modulating hydrophobic polymer. Although, the disclosure is silent about the effects of mupirocin compositions disclosed, the skin permeation results provided for tretinoin compositions showed a noticeable delivery of the active ingredient through the epidermis and, therefore, making available the active ingredient sistemically. This is a disadvantage since permeation of topical drugs through the skin can modify the safety profiles of the pharmaceutical or veterinary product, a critical feature when assessing bioequivalence between a new composition of a marketed pharmaceutical or veterinary product.

Therefore, as extracted from the state of the art exposed above, it would be desirable to have at one's disposal improved stable topical pharmaceutical or veterinary compositions of mupirocin with improved clinical effect, while maintaining suitable safety profiles for assessing bioequivalence with commercial compositions of mupirocin.

SUMMARY OF THE INVENTION

The inventors have found that a pharmaceutical or veterinary anhydrous topical gel composition of mupirocin or a pharmaceutically or veterinary acceptable salt thereof comprising a lipophilic base selected from petrolatum, medium-chain triglycerides, isopropyl myristate and mixtures thereof; a bioadhesive selected from polyvinylpyrrolidone and polymethacrylates; and a solvent selected from ethanol, propanol, and isopropanol, which is stable and shows an increased residence time of the active ingredient in the skin, resulting in an improved clinical effect on dermal infections while maintaining a suitable dermal tolerance. The increased residence time of mupirocin allows to decrease the number of applications maintaining the clinical effect, thus improving the cost/effect ratio of the treatment of topical infections with mupirocin.

Besides, the pharmaceutical or veterinary composition of the invention further complies with bioequivalence requirements regarding safety and delivery profiles. The permeation profile of murpirocin shown by the compositions of the invention is similar to that of the commercial compositions of mupirocin, Bactroban.

The pharmaceutical or veterinary composition of the present invention also complies with viscosity, physical and chemical stability and formulation requirements for topical compositions. Additionally, unlike known compositions, the composition of the invention is transparent and colorless easing patient agreement with the product and with the treatment.

Moreover, the pharmaceutical or veterinary composition of the present invention shows suitable stability and dissolution of mupirocin for complying with requirements for marketing and use of bioadhesive gels.

Although each one of above advantages of the pharmaceutical or veterinary composition of the invention is a major development in the art, their combination renders a more effective pharmaceutical composition suitable for treating topical infections due to the increased residence time of the active ingredient in the skin while assessing bioequivalence to the commercial product and complying with the viscosity, physical and chemical stability and formulation requirements for topical compositions.

Thus, as an aspect of the invention, the invention provides a pharmaceutical or veterinary anhydrous topical gel composition of mupirocin or a pharmaceutically or veterinary acceptable salt thereof comprising a lipophilic base selected from petrolatum, medium-chain triglycerides, isopropyl myristate and mixtures thereof; a bioadhesive selected from polyvinylpyrrolidone and polymethacrylates; and a solvent selected from ethanol, propanol, and isopropanol.

BRIEF DESCRIPTION OF THE DRAWINGS

FIG. 1 shows the infection pattern used on murine shoulder for the in vivo assay of the clinical effect of the composition of the invention in Example 12.

DETAILED DESCRIPTION OF THE INVENTION

In the present invention, unless explicitly stated, all percentages are given in a weight basis with regard to the total weight of the topical pharmaceutical composition.

The term "lipophilic base" is referred in the present invention as a topical composition base with strong affinity for non-polar liquids and semisolids, e.g. oils.

In a particular embodiment, the composition is a pharmaceutical composition.

Suitable lipophilic bases for use in the composition of the invention are petrolatum, medium-chain triglycerides, isopropyl myristate or their mixtures.

Medium-chain triglycerides, with CAS No. 73398-61-5, is a well known compound (cf. "*Pharmaceutical Excipients*", Medium-chain triglycerides monograph, Rowe R C, Sheskey P J, and Owen S C Editors, Pharmaceutical Press and American Pharmacists Association. Electronic version, 2006 Edition) which is defined as the fixed oil extracted from the hard, dried fraction of the endosperm of *Cocos nucifera* L. or from the dried endosperm of *Elaeis quineenis* Jacq. They comprise a mixture of triglycerides of saturated fatty acids, mainly of caprylic acid and of capric acid, and contain not less than 95% of saturated fatty acids. Medium-chain triglycerides have been used in topical pharmaceutical formulations as a component of ointments, creams, and liquid emulsions.

In a particular embodiment of the present invention, the lipophilic base is selected from petrolatum, medium-chain triglycerides, and their mixtures.

In a further particular embodiment of the present invention, the lipophilic base is selected from petrolatum, medium-chain triglycerides or isopropyl myristate. More particularly, the lipophilic base can be selected from petrolatum and medium-chain triglycerides.

In a preferred embodiment of the first aspect of the invention, the lipophilic base of the composition of the invention is medium-chain triglycerides.

In a preferred embodiment of the invention, the amount of lipophilic base in the pharmaceutical composition of the invention is comprised between 15% and 50% w/w, more preferably between 18% and 36% w/w.

In the present invention, the term "bioadhesive composition" refers to a pharmaceutical composition intended for topical use wherein the composition can adhere to a biological substrate and remain in place for an extended period of time. Generally, a bioadhesive composition is used to localize drug delivery to a specific area for local action and to increase contact time at the absorption site. "Bioadhesive excipients" or "bioadhesive" are those natural or synthetic excipients which confere to the composition the ability to adhere to biological tissue.

Suitable bioadhesive pharmaceutical excipients for the use in the compositions of the present invention are polyvinylpyrrolidone and polymethacrylates, i.e. methacrylic acid polymers and copolymers.

In a preferred embodiment of the invention the bioadhesive is polyvinylpyrrolidone.

In a preferred embodiment of the invention the amount of bioadhesive in the composition is comprised between 2% and 20% w/w, preferably between 4% and 16% w/w.

In a particular embodiment of the invention the bioadhesive is a polymethacrylate and it is present in the composition in an amount from 5% to 10% w/w. Preferably the methacrylate polymer is Eudragit L, a 1:1 copolymer of methacrylic acid and methyl methacrylate.

In a particular embodiment of the invention the bioadhesive is a polyvinylpyrrolidone and it is present in the composition in an amount from 10% to 20% w/w.

The solvent used in the composition of the invention is a pharmaceutically acceptable solvent selected from ($C_2$-$C_3$) alcohols, i.e. ethanol, propanol and isopropanol, which are suitable for dissolving mupirocin.

In a preferred embodiment of the invention the solvent is isopropanol.

In a further preferred embodiment of the invention the amount of solvent in the composition is comprised between 40% an 80% w/w, preferably between 50% and 65% w/w.

In a preferred embodiment of the present invention, the composition comprises an amount of mupirocin between 1% and 2.5% w/w, preferably 2% w/w. Although the dose of mupirocin is indicated with regard to mupirocin free acid, compositions containing pharmaceutically acceptable salts or hydrates of mupirocin are also within the scope of the invention and the dose of the active ingredient will be that equivalent to the dose of mupirocin free acid.

In a preferred embodiment of the present invention, the composition further comprises at least one additional excipient selected from the group consisting of preservative agents, antioxidative agents, buffering and pH adjusting agents.

Suitable preservatives and antioxidants for topical pharmaceutical compositions can be selected from butylated hydroxyanisole (BHA), butylated hydroxytoluene (BHT), alkyl galates, e.g. propyl or ethyl galate, methylparaben, ethylparaben, propylparaben, butylparaben and its salts, benzyl alcohol, and mixtures thereof. Additionally, the composition of the invention can comprise buffering and pH adjusting agents, for instance triethanolamine, tromethamine, and phosphate salts, e.g. monosodium, disodium, and trisodium salts.

Further, the pharmaceutical compositions of the invention can comprise flavouring and colouring agents selected from those known by the person skilled in the art, in order to improve the taste and appearance of the product.

The pharmaceutical composition of the invention can be prepared by methods known in the art for the formulation of topical gels. As an example, a pharmaceutical composition according to the invention can be prepared by dissolving mupirocin in the selected solvent under stirring. Then, the bioadhesive is added slowly under gentle stirring and, finally, stirring is maintained and the lipophilic base is added. The composition of the invention is obtained after resting for 30 minutes to one hour. Additional components can be added in separate addition steps or mixed together with the above excipients and solvents before its addition to the formulation mixture.

In a particular embodiment of the invention, the composition of the invention is defined by the following general compositions:

TABLE 1.1

| Component | Amount (w/w) |
| --- | --- |
| Mupirocin | 1% to 2.5% |
| Polyvinylpyrrolidone (Kollidon 90F) | 10% to 20% |
| Medium-chain triglycerides | 20% to 30% |
| Isopropanol | 50% to 70% |

TABLE 1.2

| Component | Amount (w/w) |
| --- | --- |
| Mupirocin | 1% to 2.5% |
| Polyvinylpyrrolidone (Kollidon 30F) | 15% to 20% |
| Medium-chain triglycerides | 20% to 30% |
| Isopropanol | 50% to 70% |

TABLE 1.3

| Component | Amount (w/w) |
| --- | --- |
| Mupirocin | 1% to 2.5% |
| Polymethacrylate (Eudragit L12.5) | 5% to 10% |
| Medium-chain triglycerides | 20% to 30% |
| Isopropanol | 50% to 70% |

TABLE 1.4

| Component | Amount (w/w) |
| --- | --- |
| Mupirocin | 1% to 2.5% |
| Polyvinylpyrrolidone (Kollidon 90F) | 10% to 20% |
| Liquid petrolatum | 20% to 30% |
| Isopropanol | 60% to 80% |

TABLE 1.5

| Component | Amount (w/w) |
| --- | --- |
| Mupirocin | 1% to 2.5% |
| Polyvinylpyrrolidone (Kollidon 90F) | 10% to 20% |
| Medium-chain triglycerides | 20% to 30% |
| Etanol | 40% to 60% |

TABLE 1.6

| Component | Amount (w/w) |
| --- | --- |
| Mupirocin | 1% to 2.5% |
| Polyvinylpyrrolidone (Kollidon 90F) | 10% to 20% |
| Medium-chain triglycerides | 15% to 25% |
| Isopropanol | 50% to 65% |
| Benzil alcohol | 1% to 5% |

Benzil alcohol is added in a further final step under mild stirring.

TABLE 1.7

| Component | Amount (w/w) |
| --- | --- |
| Mupirocin | 1% to 2.5% |
| Polyvinylpyrrolidone (Kollidon 90F) | 10% to 20% |
| Medium-chain triglycerides | 20% to 40% |
| Isopropanol | 60% to 80% |
| BHA/BHT (1/1) | 0.4% to 2% |

BHA/BHT mixture is added in a further final step under intense stirring.

TABLE 1.8

| Component | Amount (w/w) |
| --- | --- |
| Mupirocin | 1% to 2.5% |
| Polyvinylpyrrolidone (Kollidon 90F) | 10% to 20% |
| Medium-chain triglycerides | 20% to 40% |
| Isopropanol | 60% to 80% |
| Tromethamine | 0.5% to 8% |

Tromethamine is added in a further final step under stirring and constant pH.

The total sum of components in all the compositions represented by the above general formulas is 100%.

In a further preferred embodiment of the invention, the anhydrous topical gel composition of mupirocin of the present invention comprises 2% w/w of mupirocin, 12% w/w of polyvinylpyrrolidone, 21% w/w of medium-chain triglycerides, and 65% w/w of Isopropanol.

Throughout the description and claims the word "comprise" and variations of the word, are not intended to exclude other technical features, additives, components, or steps. Additional objects, advantages and features of the invention will become apparent to those skilled in the art upon examination of the description or may be learned by practice of the invention. The following examples and drawings are provided by way of illustration, and they are not intended to be limiting of the present invention. Furthermore, the present invention covers all possible combinations of particular and preferred embodiments described herein.

EXAMPLES

Example 1

Bioadhesive Topical Gel of Mupirocin

| Component | % (w/w) | Weight (g) |
| --- | --- | --- |
| Mupirocin | 2 | 2.00 |
| Kollidon 90F (PVP) | 12 | 12.00 |
| Medium-chain triglycerides | 21 | 21.00 |
| Isopropanol | 65 | 65.00 |
| Total | 100 | 100 |

2 g of mupirocin were stirred in 65 g of isopropanol until total dissolution. Then, 12 g of polyvinylpyrrolidone (Kollidon 90F) was added slowly under stirring at low r.p.m. At continuation, stirring was maintained while 21 g of medium-chain triglycerides were added. After resting from 30 minutes to one hour, 100 g of the product composition was obtained as a transparent lipogel without aggregates.

The following Examples 2 to 9 were prepared according to the above preparation process. All the compositions obtained showed suitable dissolution of mupirocin.

Example 2

| Component | % (w/w) | Weight (g) |
| --- | --- | --- |
| Mupirocin | 2 | 2.00 |
| Kollidon 90F (PVP) | 10 | 10.00 |
| Medium-chain triglycerides | 32 | 32.00 |
| Isopropanol | 56 | 56.00 |
| Total | 100 | 100 |

Example 3

| Component | % (w/w) | Weight (g) |
| --- | --- | --- |
| Mupirocin | 2 | 2.00 |
| Kollidon 90F (PVP) | 12 | 12.00 |
| Medium-chain triglycerides | 36 | 36.00 |
| Isopropanol | 50 | 50.00 |
| Total | 100 | 100 |

Example 4

| Component | % (w/w) | Weight (g) |
| --- | --- | --- |
| Mupirocin | 2 | 2.00 |
| Kollidon 90F (PVP) | 4 | 4.00 |
| Medium-chain triglycerides | 32 | 32.00 |
| Isopropanol | 62 | 62.00 |
| Total | 100 | 100 |

Example 5

| Component | % (w/w) | Weight (g) |
| --- | --- | --- |
| Mupirocin | 2 | 2.00 |
| Kollidon 90F (PVP) | 12 | 12.00 |
| Medium-chain triglycerides | 18 | 18.00 |
| Benzyl alcohol | 3 | 3.00 |
| Isopropanol | 65 | 65.00 |
| Total | 100 | 100 |

The composition of Example 5 was obtained according to the process described for Example 1, further adding 3 g of benzyl alcohol after the addition of the medium-chain triglycerides.

Example 6

| Component | % (w/w) | Weight (g) |
| --- | --- | --- |
| Mupirocin | 2 | 2.00 |
| Kollidon 90F (PVP) | 12 | 12.00 |
| Medium-chain triglycerides | 23 | 23.00 |
| Benzyl alcohol | 3 | 3.00 |
| Isopropanol | 60 | 60.00 |
| Total | 100 | 100 |

The composition of Example 6 was obtained according to the process of Example 5.

Example 7

| Component | % (w/w) | Weight (g) |
| --- | --- | --- |
| Mupirocin | 2 | 2.00 |
| Kollidon 90F (PVP) | 16 | 16.00 |
| Medium-chain triglycerides | 20 | 20.00 |
| Benzyl alcohol | 2 | 2.00 |
| Isopropanol | 60 | 60.00 |
| Total | 100 | 100 |

The composition of Example 7 was obtained according to the process of Example 6.

Example 8

| Component | % (w/w) | Weight (g) |
| --- | --- | --- |
| Mupirocin | 2 | 2.00 |
| Kollidon 90F (PVP) | 16 | 16.00 |
| Medium-chain triglycerides | 22 | 22.00 |
| Isopropanol | 60 | 60.00 |
| Total | 100 | 100 |

Example 9

| Component | % (w/w) | Weight (g) |
| --- | --- | --- |
| Mupirocin | 2 | 2.00 |
| Kollidon 90F (PVP) | 16 | 16.00 |
| Eudragit L12.5 (polymethacrylates) | 1 | 1.00 |
| Medium-chain triglycerides | 19 | 19.00 |
| Benzyl alcohol | 2 | 2.00 |
| Isopropanol | 60 | 60.00 |
| Total | 100 | 100 |

The composition of Example 9 was obtained according to the process described for Example 5, further adding 1 g of Eudragit L 12.5 under stirring after the dissolution of mupirocin.

Comparative Example 10

Two hydrophilic compositions were formulated to test the viability of bioadhesive hydrophilic gel bases. Both compositions were obtained according to the process of Example 1 but adding propyleneglycol instead medium-chain triglycerides.

Comparative Hydrophilic Composition A

| Component | % (w/w) | Weight (g) |
|---|---|---|
| Mupirocin | 2 | 2.00 |
| Kollidon 90F (PVP) | 10 | 10.00 |
| Propyleneglycol | 32 | 32.00 |
| Isopropanol | 56 | 56.00 |
| Total | 100 | 100 |

Comparative Hydrophilic Composition B

| Component | % (w/w) | Weight (g) |
|---|---|---|
| Mupirocin | 2 | 2.00 |
| Kollidon 90F (PVP) | 12 | 12.00 |
| Propyleneglycol | 36 | 36.00 |
| Isopropanol | 50 | 50.00 |
| Total | 100 | 100 |

Composition A was obtained as a very fluid hydrogel with a very high absorption of air. After resting for some hours aggregates of mupirocin appeared indicating that the active ingredient precipitates.

Composition B was obtained as a very viscous hydrogel with aggregates which was homogenized for 15 minutes and an homogeneous gel was obtained. However, after resting overnight the composition showed turbidity and aggregates due to the precipitation of the components.

Example 11

Transdermal Permeation Assay of Mupirocin Compositions

The transdermal permeation assay was carried out in accordance to "Guidance document for the conduct of skin absorption studies" OECD series on testing assessment, No. 28 ENV/JM/MONO (2004) 2.5 Mar. 2004.

Compositions of Example 1 and Example 2 were assayed together with Bactroban Ointment, which is the commercial product and it is included as comparative product.

Franz cells were used with a diameter of 1.8 cm and an area of 2.54 $cm^2$. Abdominal human skin with a thickness of 0.4 mm was used as permeation membrane. Skin was obtained from reconstructive surgery and it was treated before use. Integrity of the selected skin was checked by the transepidermal water loss value. Each composition was assayed in a population (n=6) of skin membranes from different origins to be representative of a collective providing interindividual variation.

300 mg of the assayed composition were placed in the donor chamber. Hydroalcoholic solution 80:20 v/v, maintained at 32±1° C. by jacketed heater, was used as receptor fluid. Sampling was carried out from the receptor chamber at the following sampling times: 2, 4, 8, and 12 h. Sample volume was 0.3 ml.

4 assays were carried out with 18 cells per assay. A fifth assay with 12 cells was performed only at 12 h on placebo compositions. Samples were conserved at −20° C. until HPLC/UV titration for mupirocin (Column: LiChrosper® 60RP-select B (5 µm) 250 mm×4 mm; Eluent: acetonitrile: ammonium acetate 0.05 M, pH 6.3 (27.5:72.5); flux rate 1 ml/min)

TABLE 2

Permeation data for Example 1 at 12 h.

| Cell | Mupirocin permeated through human skin (% w/w) |
|---|---|
| 1 | 0.0500 |
| 2 | 0.0187 |
| 3 | 0.0048 |
| 4 | 0.0000 |
| 5 | 0.0000 |
| 6 | 0.0000 |
| Median | 0.0024 |

TABLE 3

Permeation data for Bactroban at 12 h.

| Cell | Mupirocin permeated through human skin (% w/w) |
|---|---|
| 7 | 2.4442 |
| 8 | 0.0000 |
| 9 | 0.0000 |
| 10 | 0.0000 |
| 11 | 0.0000 |
| 12 | 0.0000 |
| Median | 0.0000 |

TABLE 4

Permeation data for Example 2 at 8 h and 12 h.

| Cell | Mupirocin permeated through human skin (% w/w) | |
|---|---|---|
|  | 8 h | 12 h |
| 13 | 0.0000 | 0.0000 |
| 14 | 0.0000 | 0.0000 |
| 15 | 0.1042 | 0.2997 |
| 16 | 0.0000 | 0.0000 |
| 17 | 0.0000 | 0.0000 |
| 18 | 0.0000 | 0.0000 |
| Median | 0.0000 | 0.0000 |

Permeation data is provided as percentage in weight of mupirocin permeated with regard to total weight of mupirocin in the assayed composition. Median value is shown to provide a location parameter of the measures due to the variability of the biological samples.

Data obtained were treated by a Kruskall-Wallis non-parametrical statistical test to evidence differences on the permeation of mupirocin from the three assayed compositions at 12 h. Dunn's multiple comparison test was also performed to identify which compositions showed said differences. Table 5 shows the results of the stadistical analysis.

TABLE 5

| % PERM 12 H Kruskal-Wallis test | Value |
|---|---|
| P value | 0.5648 |
| Exact or approximate P value? | Gaussian Approx. |
| P value summary | ns |
| Do the medians vary signif.? (P < 0.05) | No |
| Number of groups | 3 |
| Kruskal-Wallis statistic | 1.143 |

| Dunn's Multiple Comparison Test | Difference in rank sum | Summary |
|---|---|---|
| Example 1 vs. Bactroban | 2.167 | ns (P > 0.05) |
| Example 1 vs. Example 2 | 2.333 | ns (P > 0.05) |
| Bactroban vs. Example 2 | 0.1667 | ns (P > 0.05) | ns = Not significant

In conclusion, according to the results of the transdermal permeation assay, the amount of mupirocin permeated through human skin 12 hours after administration of the compositions of the invention was not relevant nor showed differences for the assayed compositions. Therefore, the assayed compositions show a similar systemic safety profile, which is also similar to Bactrobran, which is the commercial product and it is included as comparative product.

Residence of Mupirocin in Skin at 8 h.

Skin membranes used in permeation assays at 8 h were washed with a 0.1% sodium lauryl sulfate solution, then skin was dryed and weighted. To extract mupirocin, skin was submerged in a 50:50 v/v hydroalcoholic solution for 20 minutes under sonication and constant temperature.

TABLE 6 skin residence of mupirocin after 8 h
Mupirocin extracted from human skin (median % w/w)

| Example 1 | Example 2 | Bactroban |
|---|---|---|
| 0.049 | 0.062 | 0.000 |

Data obtained were treated by a Kruskall-Wallis non-parametrical statistical test to evidence differences on the residence in the skin of mupirocin from the assayed compositions after 8 h. Dunn's multiple comparison test was also performed to identify which compositions showed said differences. Data of mupirocin extracted from human skin is provided as percentage in weight of mupirocin extracted with regard to total weight of mupirocin in the assayed composition. Table 7 shows the results of the stadistical analysis.

TABLE 7

| % EXTR 8 H Kruskal-Wallis test | Value |
|---|---|
| P value | 0.0027 |
| Exact or approximate P value? | Gaussian Approx. |
| P value summary | ** |
| Do the medians vary signif, (P < 0.05) | Yes |
| Number of groups | 3 |
| Kruskal-Wallis statistic | 11.8 |

| Dunn's Multiple Comparison Test | Difference in rank sum | Summary |
|---|---|---|
| Example 1 vs. Bactroban | 8.333 | * (P > 0.05) |
| Example 1 vs. Example 2 | −1.333 | ns (P > 0.05) |
| Bactroban vs. Example 2 | −9.667 | ** (P < 0.01) | ns: not significant
* significant
** very significant

In conclusion, according to the results of the residence assay, the amount of mupirocin remaining in human skin 8 hours after administration of the compositions of the invention was significantly higher than the amount remaining after the administration of Bactroban ointment.

High value of the drug residence in skin at 8 hours from application is advantageous in an administration regime of three applications a day because at eight hours, when the product is applicated again, the amount of drug remaining in the skin from the first application is higher, resulting in a more constant drug residence. Thus, the compositions of the present invention allow to decrease the number of applications maintaining the clinical effect and improving the cost/effect ratio of the treatment of topical infections with mupirocin.

Example 12

In Vivo Effect of Mupirocin Compositions

In vivo effect of the composition of Example 1 and Bactroban was assayed in a murine model of *S. aureus* infection based in Gisby et al., "Efficacy of a new cream formulation of mupirocin: comparison with oral and topical agents in experimental skin infections." *Antimicrob. Agents Chemother.*, vol. 44, pp. 255-260.

*S. aureus* strains were isolated from human patients suffering from faringeous infection or infected wounds which showed to be sensible to mupirocin in antimicrobial sensibility tests. The suture thread used as sterile support was soaked in the suspension of microorganisms obtained from the isolated strain before its application to the animals. The surgical procedure used to induce infection on the assayed rats is shown in FIG. 1.

Two points were marked in the medium line of Z1 with a separation of 1 cm between them. The infected thread was inserted through one of them and emerged from the other. Then, thread was cut as close as possible to the skin in both marked points and the thread was pulled in both senses of the thread direction. Thus, both ends of the thread were inserted in the skin. Finally, an straight incision was made along the length between the marked points and a single stich was sutured in the middle when needed. The same procedure was followed in Z3, leaving uninfected Z2 for its use as control.

Two groups of 10 animals were treated, one with Composition of Example 1 and the other with Bactroban. The assayed compositions were administered three times a day during four days. The whole wounded area was covered after the administration of the corresponding composition.

The colony founder units count after the treatment is shown below for both compositions:

TABLE 8

| | *Staphylococcus aureus* (Ufc) | |
|---|---|---|
| Animal | Bactroban | Example 1 |
| 1 | 1.17E+03 | 0.00E+00 |
| 2 | 0.00E+00 | 0.00E+00 |
| 3 | 2.79E+03 | 0.00E+00 |
| 4 | 7.20E+02 | 6.30E+02 |
| 5 | 2.04E+05 | 2.70E+02 |
| 6 | 4.32E+06 | 4.14E+03 |
| 7 | 4.05E+06 | 3.60E+03 |
| 8 | 2.70E+02 | 3.24E+03 |
| 9 | 5.58E+03 | 0.00E+00 |
| 10 | 1.17E+04 | 1.09E+05 |
| Mean | 3.10 | 2.10 |

According to the results, the count of colony founder units is significantly lower in the case of the wounds treated with the composition of the invention. Therefore, the treatment with the bioadhesive gel of the invention is significantly more effective than the treatment with Bactroban. Additionally, the animals showed a very good tolerance to the treatment with the composition of Example 1 despite the increased residence time and clinical effect of the composition of the invention.

REFERENCES CITED IN THE APPLICATION

"*Guidance document for the conduct of skin absorption studies*" OECD series on testing assessment, No. 28 ENV/JM/MONO (2004) 2.5 Mar. 2004

"*Guidance for industry, nonsterile semisolid dosage forms*" SUPAC May 1997

Gisby et al., "Efficacy of a new cream formulation of mupirocin: comparison with oral and topical agents in experimental skin infections." *Antimicrob. Agents Chemother.*, vol. 44, pp. 255-260.

"*Pharmaceutical Excipients*", Medium-chain triglycerides monography, Rowe R C, Sheskey P J, and Owen S C Editors, Pharmaceutical Press and American Pharmacists Association. Electronic version, 2006 Edition

EP0251434A2
EP1174133A1
WO199823291A1
WO200410988A1

The invention claimed is:

1. A pharmaceutical or veterinary composition which comprises
   2% w/w Mupirocin;
   12% w/w Polyvinylpyrrolidone;
   21% w/w Medium-chain triglycerides; and
   65% w/w Isopropanol.

* * * * *